United States Patent
Konoshima et al.

Patent Number: 5,414,015
Date of Patent: May 9, 1995

[54] ANTI-SKIN TUMOR PROMOTING COMPOSITION

[75] Inventors: Takao Konoshima; Harukuni Tokuda, both of Kyoto; Munekazu Iinuma; Mizuo Mizuno, both of Gifu, all of Japan

[73] Assignee: Tsujimoto Kagaku Kogyo Co., Ltd., Osaka, Japan

[21] Appl. No.: 2,091

[22] Filed: Jan. 8, 1993

Related U.S. Application Data

[63] Continuation of Ser. No. 859,165, Mar. 27, 1992, abandoned.

[30] Foreign Application Priority Data

Jul. 23, 1991 [JP] Japan .................. 3-207634

[51] Int. Cl.$^6$ .......................... A61K 31/35
[52] U.S. Cl. ........................... 514/456
[58] Field of Search ..................... 514/456

[56] References Cited
PUBLICATIONS

Nagal et al., Chem. Pharm. Bull. 38(5) 1329–1332 (1990, May).
Natural Pharmaceitical Magazine, pp. 343–346, Japan, "Studies on Inhibitory Effects of Flavonoids on Epstein–Barr Virus Activation (1)", Jun. 18, 1988.
Natural Pharmaceutical Magazine, pp. 135–141, Japan, "Studies on Inhibitors of Skin Tumor Promotion (V), Inhibitory Effects of Flavonoids on Epstein–Barr Virus Activation. 11", Oct. 17, 1988.

*Primary Examiner*—Jerome D. Goldberg
*Attorney, Agent, or Firm*—Thompson, Hine and Flory

[57] ABSTRACT

An anti-skin tumor promotor comprising a compound of the general formula

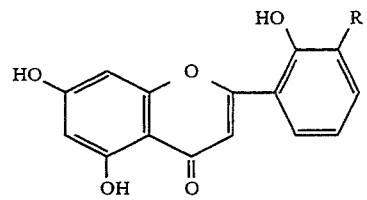

wherein R means a hydrogen atom or a hydroxyl group. The promotor may be an extract of the crude drug Scutellaria or a synthetic compound.

3 Claims, 2 Drawing Sheets

ANTI-SKIN TUMOR PROMOTING COMPOSITION

This is a CONTINUATION of application Ser. No. 07/859,165, filed Mar. 27, 1992, now abandoned.

BACKGROUND OF THE INVENTION

1. Field of the Invention

The present invention relates to an anti-skin tumor promoting composition based on a herbal extract, which is used as an anti-skin tumor functional substance chiefly active against expression of the genetic material involved in carcinogenesis.

2. Description of the Prior Art

The conventional anti-tumor agents are invariably intended to resolve the outcome of an oncogenic process, namely killing tumor cells. Accordingly, different antitumor agents are required according to different sites and stages of tumor, thus lacking in universality. On the thought that inhibiting the transformation of normal cells into tumor cells is more reasonable than killing tumor cells, the inventors of the present invention focused attention on the process of oncogenesis which, unless arrested, would lead to the ultimate neoplastic form. Thus, it is well known that a normal cell experiences the two different stages of initiation and promotion before it is established as a genuine tumor cell. Of these stages, the initiation stage is governed by factors varying with different hosts but the promotion stage follows a comparatively uniform course. Therefore, it is more universal, as a mode of approach, to suppress this process of promotion. This means that should we be able to provide an effective anti-skin tumor promotor drug, the medical profession should be better and greatly rewarded.

SUMMARY OF THE INVENTION

The inventors of the present invention previously disclosed that amoung various flavonoids occurring in herbal drugs, afromosin, formononetin, ononin and wistin, all belonging to the class of isoflavonoids, have anti-tumor promotor activity (The 7th Symposium on the Development and Application of Natural Drugs, Jul. 28, 1989, Fukuoka, sponsored by Pharmaceutical Society of Japan). The inventor further reported on an EBV-EA (Epstein-Barr virus early antigen) activation inhibition test, a primary screening for anti-tumor promotor substances, which was performed using about 80 different flavonoids (The Japanese Journal of Pharmacognosy 43 (2), 135-141, 1989).

In the former investigation, the efficacy of various isoflavonoids as anti-tumor promotors has been demonstrated both in vitro and in animal experiments. In the latter investigation, although a large number of flavonoids were screened, no attempt was made to identify specific compounds which can be direct anti-tumor promotors.

The object of the present invention is to identify, among various flavonoids occurring in Scutellaria, a well-known crude drug, specific compounds having potent anti-skin tumor promotor activity and to provide an effective anti-skin tumor promotor composition.

The above object was accomplished by the present invention which provides an anti-skin tumor promotor composition based on a compound of the general formula

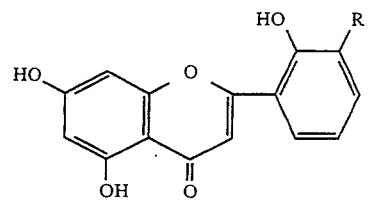

wherein R means a hydrogen atom or a hydroxyl group.

Furthermore, the above object was accomplished by the invention which provides a compound of the above formula by chemical synthesis.

Further objects, features and advantages of the present invention will become apparent as the following detailed discussion referring to the accompanying drawings proceeds.

DESCRIPTION OF THE PREFERRED EMBODIMENTS

Figure 1:
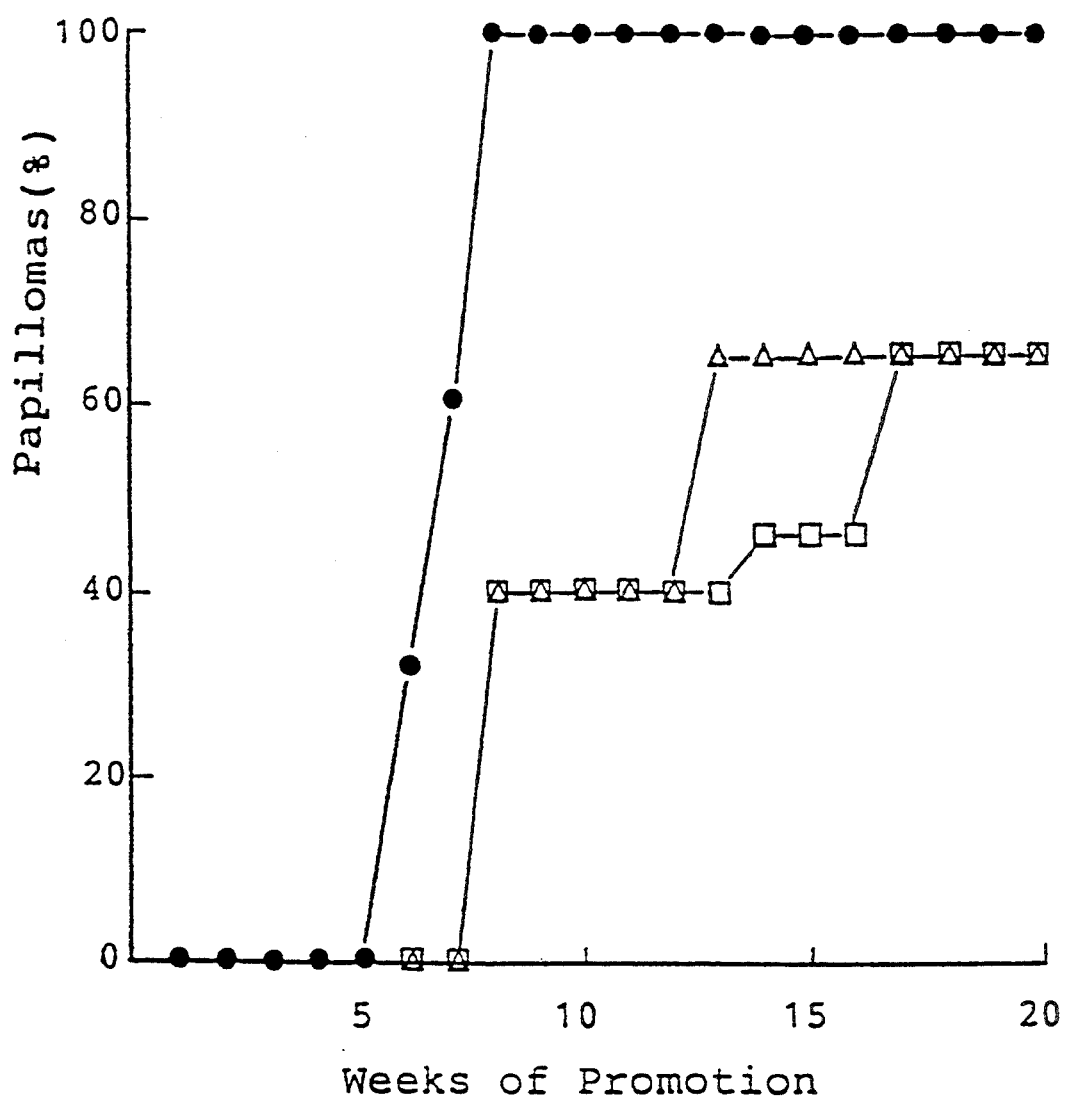
FIG. 1 is a diagrammatic representation of the results of an animal experiment using flavonoids of the invention.

The two compounds of the above general formula are either the natural substances which are among many flavonoids isolated from Scutellaria or synthetic compounds of the same chemical structures. These compounds as well as 34 other representative flavonoids, natural or synthetic, were subjected to EBV-EA primary screening and found to have high inhibitory activity. The results of this primary screening using a total of 36 flavonoids are presented in Tables 1 through 4. In the tables, compounds No. 34 and No. 35 are 5,7,2'-trihydroxyflavone and 5,7,2',3'-tetrahydroxyflavone, respectively, both of which are anti-skin tumor promotors of the invention.

For said primary screening, a latent EBV infected human lymphoblastoid cell line Raji was provided in a concentration of $1 \times 10^6$ cells/ml, and 4 mM butyric acid and 20 ng/ml TPA (12-0-tetradecanoylphorbol-13-acetate) in DMSO were added. The mixture was incubated at 37° C. for 48 hours and the EBV-EA was stained by the indirect fluorescence antibody method using the serum from a patient with cancer of epipharynx. The incidence of positive cells was regarded as 100% and used as positive control. As to the incidence of positive cells in test samples, the same amounts of butyric acid and TPA as above and a varying concentration of the test substance were added to suspensions of the Raji cell line and, after cultivation, the percentage of positive cells in each case was calculated in the same manner. The concentration was expressed as mol/TPA (20 ng=32 pmol/ml). Of the data corresponding to each concentration, the figure at left is the percentage of positive control and the figure in brackets at right represents the survival rate of Raji cells.

From the results of the primary screening as shown in Tables 1 through 4, No. 34 (5,7,2'-trihydroxyflavone) and No. 35 (5,7,2',3'-tetrahydroxyflavone) were chosen for the following reasons. Thus, since too small a survival rate figure in brackets means that normal cells are also killed, the corresponding substance should be culled out. Therefore, substances giving survival rates not less than 60% were first selected. Then, because the efficacy will be low across the board at too low a sample concentration, the data at concentrations $1\times 10$ and $1\times 10^2$ were excluded and only the data at $5\times 10^2$ and $1\times 10^3$ were evaluated. As a result, compounds No. 34 and No. 35 which can be extracted from Scutellaria extract and can be synthesized as well were ultimately chosen. These compounds, viz. 5,7,2'-trihydroxyflavone and 5,7,2',3'-tetrahydroxyflavone, gave higher cell survival rates than Scutellaria extract which has been considered to have anti-tumor promotor activity. Therefore, these two substances were considered to be active principles of Scutellaria extract. Compound No. 24, a synthetic flavonoid, also gave satisfactory values but since the survival rates of Raji cells were extremely low at high concentrations and the inhibitory activity was low at low concentrations, its inhibitory potential could not be estimated. Thus, 5,7,2'-trihydroxyflavone of the formula

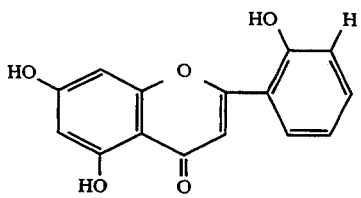

and 5,7,2',3'-tetrahydroxyflavone of the formula

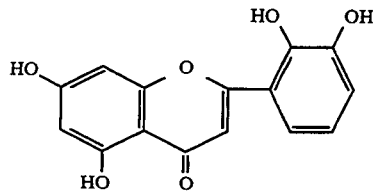

are two flavones ultimately selected from among the flavonoids occurring in the crude drug Scutellaria.

A typical method for extraction and purification of these two substances from Scutellaria is now described. Thus, 1 kg of scutellaria root is pulverized and extracted with acetone under reflux and the extract is concentrated. The residue is chromatographed on a silica gel column and elusion is carried out with chloroform-methanol. The fractions rich in 5,7,2'-trihydroxyflavone and those rich in 5,7,2',3'-tetrahydroxyflavone were respectively pooled. The process of elusion was monitored by thin-layer chromatography. The eluates thus obtained were respectively recrystallized to give 5,7,2'-trihydroxyflavone as light yellow platelets and 5,7,2',3'-tetrahydroxyflavone as light yellow needles.

A typical method for chemical synthesis of 5,7,2'-trihydroxyflavone is now described. Thus, floroacetophenone diisopropyl ether (1.8 g, 7 mmol) and 2-isopropoxybenzaldehyde (2.4 g, 15 mmol) are dissolved in 80% (v/v) ethanol (50 ml) containing sodium hydroxide (2 g) and the solution is allowed to stand overnight. The reaction mixture is then acidified with hydrochloric acid and extracted with ethyl acetate to give 2'-hydroxy-2,4',6'-triisopropoxychalcone (2.3 g) as orange-colored platelets. This product has a melting point of 119°-120° C. (methanol). The above chalcone (800 mg, 2 mmol) is dissolved in ethanol (50 ml) containing phosphoric acid (4 g) and the solution is refluxed for 30 hours. The reaction mixture is then diluted with water and extracted with ethyl acetate to give a light yellow oil (750 mg). This oil (300 mg) is dissolved in dioxane (10 ml) followed by addition of dichlorodiaminobenzoquinone (DDQ) (250 mg, 1.1 mmol) and the mixture is refluxed for 3 hours. The reaction mixture is cooled and the reduced substance is filtered off. The filtrate is purified by silica gel column chromatography (eluent=chloroform) to give 5,7,2'-triisopropoxyflavone (240 mg) as a brown oil. Finally this brown oil (230 mg) is dissolved in dichloromethane and after the solution is cooled to $-70°$ C., boron trichloride (0.5 ml) is added. The mixture is allowed to stand at room temperature for 1 hour, after which it is poured in water and extracted with ethyl acetate to give 120 mg of 5,7,2'-trihydroxyflavone as light yellow platelets.

The physical properties of 5,7,2'-trihydroxyflavone thus obtained are as follows.

Melting point 279° C. (acetone)

$^1$H-nuclear magnetic resonance spectrum (DMSO-$d_6$): 6.22, 6.48 (2 H, each d, J=1.8 Hz, H-6, 8), 6.93–7.40 (3 H, m, H-3',4',5'), 7.85 (1 H, dd, J=7.5, 2.0 Hz, H-6'), 10.70 (2 H, br s, OH), 12.80 (1 H, br s, OH)

Electron impact mass spectrum m/z (%): 270 [M+] (100), 242 (13), 153 (23), 152 (33), 124 (20), 121 (16), 118 (11)

Ultraviolet absorption spectrum (methanol) λmax: 267, 338 (nm)

A typical method for synthesis of 5,7,2',3'-tetrahydroxyflavone is now described. Substantially in the same manner as the production of 5,7,2'-trihydroxyflavone, floroacetophenone diisopropyl ether (650 mg, 2.7 mmol) is reacted with 2,3-diisopropoxybenzaldehyde (600 mg, 2.7 mmol) and the resulting condensation product is subjected to oxidation with DDQ and elimination of the protective group to give 5,7,2',3'-tetrahydroxyflavone as light yellow powdery crystals.

The physical properties of 5,7,2',3'-tetrahydroxyflavone are as follows.

Melting point 327° C. (decomp.) (acetone-benzene)

$^1$H-nuclear magnetic resonance spectrum: 6.22, 6.46 (2 H, each d, J=2.3 Hz, H-5'), 7.03 (1 H, dd, J=7.5, 2.0 Hz, H-4'), 7.04 (1 H, s, H-3), 7.32 (1 H, dd, J=7.5, 2.0 Hz, H-6'), 10.05 (3 H, br s, OH x 3), 12.88 (1 H, s, C$_5$—OH)

Electron impact mass spectrum m/z (%): 286 [M+] (100), 153 (88), 134 (18)

Ultraviolet absorption spectrum: 266, 294 sh, 332 (nm)

The anti-skin tumor promotor of the present invention, whether isolated from Scutellaria extract or synthesized, can be administered orally or otherwise in various dosage forms such as capsules, tablets, injections, etc. which are per se known. The dosage is dependent on the patient's age, body weight and condition, among other factors. Generally, for oral administration to an adult human, the daily dosage can be chosen and adjusted within the range of 1 to 200 mg. Preferably, 5 to 80 mg is repeatedly administered daily.

Regarding the toxicity of the anti-skin tumor promotor of the present invention, there is substantially no cause of concern, for it is a substance extracted from the time-honored crude drug Scutellaria or a synthetic equivalent.

It has been demonstrated in animal experiments that the repeated administration or intake of the anti-skin tumor promotor of the present invention suppresses the risk of the neoplasmic change of normal cells to a minimum, indicating marked pharmacolgic efficacy, Moreover, because it is a component of the crude drug Scutellaria, this anti-skin tumor promoting agent has no acute toxicity. There is no safety hazard even in repeated administration, which is rather desirable for inhibition of the onset of cancer. The prophylactic nature of this anti-skin tumor promoting agent makes it a functional food as well.

EXAMPLE 1

An experiment was performed using 6-week-old female ICR mice caged in groups of 5 individuals. The animals were allowed free access to solid food and water. The back of each mouse, at 6 weeks of age, was clipped of hair and on the following day, i.e. after 24 hours, a two-stage carcinogenesis experiment was carried out. Thus, an acetone solution of dimethylbenzanthracene (DMBA), adjusted to a concentration of 100 μg/0.1 ml (390 nml), was applied from a pipet to the clipped back. After one week, 85 nmol 5,7,2′-trihydroxyflavone or 5,7,2′,3′-tetrahydroxyflavone in acetone was applied to the same site. After a further 1 hour, 1.7 nml of an acetone solution of the tumor promotor TPA (1 μg TPA/0.1 ml) was similarly applied. The above procedure was performed twice a week for 20 consecutive weeks and the inhibitory effect of treatment on skin tumor promotion was investigated.

Figure 2:
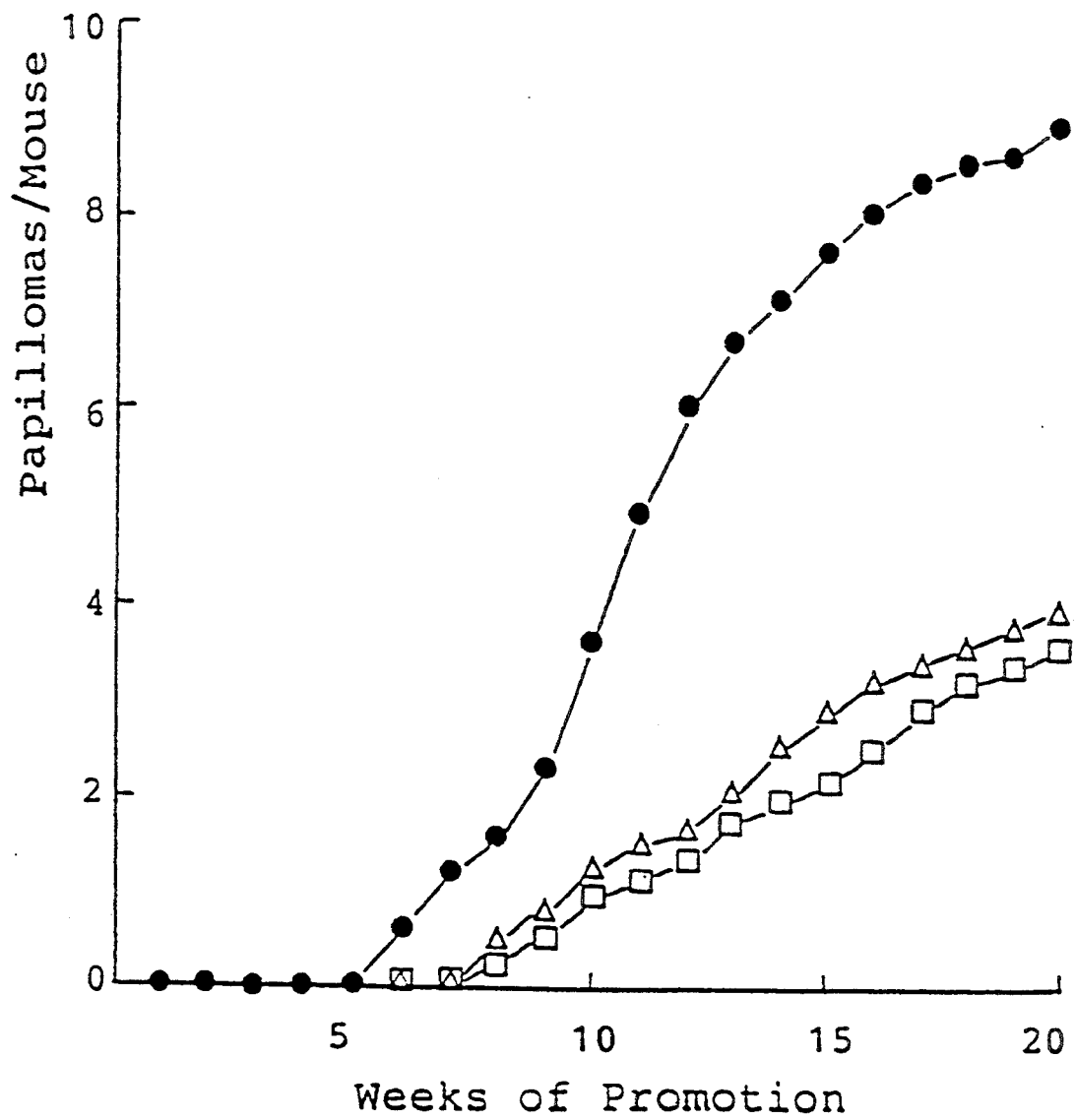
FIG. 2 is a similar diagram.

The results were evaluated once a week for papillomas 1 mm or larger in diameter in terms of the percentage of the number of tumor-bearing mice relative to the number of test mice and in terms of the number of tumors that appeared per mouse. As a positive control, acetone in lieu of the test compound was applied. The percentage of tumor-bearing mice relative to the total number of test mice is shown in FIG. 1, while the number of papillomas per mouse is shown in FIG. 2. In FIG. 1, the age in weeks of the promoted mice is plotted on the abscissa and the percentage of skin tumor-bearing mice relative to the number of test mice is plotted on the ordinate. In FIG. 2, the age of mice is similarly plotted on the abscissa, while the number of papillomas appearing per mouse is plotted on the ordinate. In these figures, the graph plotted in solid circles represents a control group not treated with any anti-skin tumor promotor; the graph plotted in triangles represent the group treated with the 5,7,2′-trihydroxyflavone solution and the group plotted in squares represent the group treated with the 5,7,2′,3′-tetrahydroxyflavone solution.

It is apparent from FIG. 1 that whereas the onset of skin tumor occurred in all cases at week 8 in the control group of mice not treated with any anti-skin tumor promotor, the two groups of mice treated with the anti-skin tumor promoting agents of the invention showed an inhibition rate of 60%. Moreover, even at week 11 of age, no neoplasma was found in 25% of the treated mice. It is also apparent from FIG. 2 that whereas the number of skin tumors showed a sharp increase after week 5 of age in the untreated group, the groups treated with the anti-skin tumor promoting agents of the invention showed only a moderate increase in the number of papillomas even in the mice found to be tumor-bearing, indicating that the anti-skin tumor promotors of the invention have definite anti-skin tumor promoting activity.

The two anti-skin tumor promoting agents, 5,7,2′-trihydroxyflavone and 5,7,2′,3′-tetrahydroxyflavone, which are provided by the invention, have prophylactic functions as anti-skin tumor promotors and are, therefore, not amenable to clinical trials. However, the results of animal experiments in mice suggest that they are very effective anti-skin tumor promotors.

It should be understood that the above example is merely intended to illustrate the technical features of the invention and should by no means be construed as defining the metes and bounds of the invention. It is, therefore, obvious that many changes and modifications may be made by those skilled in the art without departing from the spirit and scope of the appended claims.

TABLE 1

| Compound | 4′ | 6′ | 2 | 6 | Concentration$^{a)}$ | | | |
|---|---|---|---|---|---|---|---|---|
| | | | | | $1 \times 10^3$ | $5 \times 10^2$ | $1 \times 10^2$ | $1 \times 10$ |
| 1 | H | OMe | OCH(CH$_3$)$_2$ | H | 6.6$^{b)}$ (70)$^{c)}$ | 63.5 (80) | 74.6 (80) | 98.4 (80) |
| 2 | OCH$_2$Ph | OCH$_2$Ph | OMe | H | 53.2 (80) | 66.6 (80) | 87.0 (80) | 100.0 (80) |
| 3 | OCH(CH$_3$)$_2$ | OCH(CH$_3$)$_2$ | OMe | H | 27.3 (80) | 64.8 (80) | 85.3 (80) | 100.0 (80) |
| 4 | OCH$_2$Ph | OCH$_2$Ph | OCH$_2$Ph | H | 41.9 (80) | 58.1 (80) | 90.2 (80) | 100.0 (80) |
| 5 | OCH$_2$Ph | H | OCH$_2$Ph | OMe | 41.6 (70) | 90.2 (80) | 100.0 (80) | 100.0 (80) |
| 6 | OCH$_2$Ph | OCH$_2$Ph | OCH(CH$_3$)$_2$ | H | 48.6 (70) | 71.4 (80) | 100.0 (80) | 100.0 (80) |
| 7 | OMe | OMe | OCH$_2$Ph | H | 17.4 (70) | 31.6 (80) | 74.2 (80) | 100.0 (80) |
| 8 | OCH(CH$_3$)$_2$ | OCH(CH$_3$)$_2$ | OCH(CH$_3$)$_2$ | H | 34.8 (80) | 59.1 (80) | 71.4 (80) | 100.0 (80) |

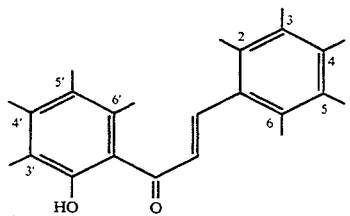

$^{a)}$Mol ratio/TPA (20 ng = 32 pMol/ml)
$^{b)}$Values represent relative percentages to the positive control value (100%).
$^{c)}$Values in parentheses are viability percentages of Raji cells.

TABLE 2

| Comp. | 5 | 7 | 2′ | 3′ | Concentration$^{a)}$ | | | |
|---|---|---|---|---|---|---|---|---|
| | | | | | $1 \times 10^3$ | $5 \times 10^2$ | $1 \times 10^2$ | $1 \times 10$ |
| 9 | OCH(CH$_3$)$_2$ | OCH(CH$_3$)$_2$ | OMe | H | 16.6$^{b)}$ (80)$^{c)}$ | 50.2 (80) | 78.4 (80) | 100.0 (80) |
| 10 | OH | OH | OH | H | 55.1 (60) | 73.6 (80) | 100.0 (80) | 100.0 (80) |

TABLE 2-continued

| Comp. | 5 | 7 | 2' | 3' | 1 × 10³ | 5 × 10² | 1 × 10² | 1 × 10 |
|---|---|---|---|---|---|---|---|---|
| | | | | | | Concentration[a] | | |
| 11 | OCH(CH₃)₂ | OCH(CH₃)₂ | OCH(CH₃)₂ | H | 40.6 (80) | 65.2 (80) | 80.4 (80) | 100.0 (80) |
| 12 | OH | OH | OMe | H | 41.3 (80) | 100.0 (80) | 100.0 (80) | 100.0 (80) |
| 13 | OCH(CH₃)₂ | OCH(CH₃)₂ | OCH(CH₃)₂ | OCH(CH₃)₂ | 45.6 (80) | 64.6 (80) | 90.2 (80) | 100.0 (80) |

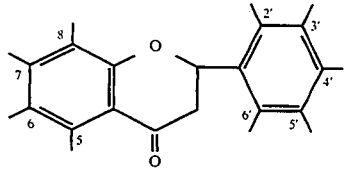

[a] Mol ratio/TPA (20 ng = 32 pMol/ml)
[b] Values represent relative percentages to the positive control value (100%).
[c] Values in parentheses are viability percentages of Raji cells.

TABLE 3

| Comp. | 3 | 5 | 7 | 2' | 3' | 5' | 6' | 1 × 10³ | 5 × 10² | 1 × 10² | 1 × 10 |
|---|---|---|---|---|---|---|---|---|---|---|---|
| | | | | | | | | | Concentration[a] | | |
| 14 | H | OH | OH | OMe | H | H | H | 18.4[b] (80)[c] | 68.7 (80) | 81.6 (80) | 100.0 (80) |
| 15 | OH | H | H | OCH(CH₃)₂ | H | H | H | 13.4 (70) | 23.3 (80) | 56.6 (80) | 85.1 (80) |
| 16 | OH | H | H | OH | H | H | H | 37.8 (70) | 69.5 (80) | 84.3 (80) | 100.0 (80) |
| 17 | OH | H | H | OCH₂Ph | H | H | H | 22.5 (70) | 43.8 (80) | 66.4 (80) | 85.8 (80) |
| 18 | OMe | H | H | OH | H | H | H | 34.1 (70) | 81.3 (80) | 100.0 (80) | 100.0 (80) |
| 19 | OMe | H | H | OCH₂Ph | H | H | H | 48.2 (70) | 61.6 (80) | 79.1 (80) | 90.5 (80) |
| 20 | OH | H | H | OMe | H | H | H | 40.1 (80) | 76.2 (80) | 100.0 (80) | 100.0 (80) |
| 21 | OH | H | H | OCH(CH₃)₂ | H | H | OCH(CH₃)₂ | 35.6 (80) | 89.3 (80) | 100.0 (80) | 100.0 (80) |
| 22 | H | OH | OH | OH | H | OH | H | 4.7 (80) | 48.3 (80) | 92.9 (80) | 100.0 (80) |
| 23 | H | H | H | OH | OMe | H | H | 28.5 (80) | 81.6 (80) | 100.0 (80) | 100.0 (80) |
| 24 | OH | OH | OH | OH | H | H | H | 0.0 (20) | 12.1 (20) | 90.2 (70) | 100.0 (80) |

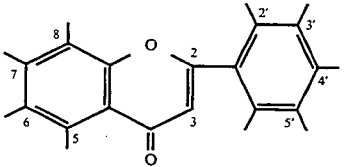

[a] Mol ratio/TPA (20 ng = 32 pMol/ml)
[b] Values represent relative percentages to the positive control values (100%).
[c] Values in parentheses are viability percentages of Raji cells.

TABLE 4

| Comp. | 3 | 5 | 7 | 2' | 3' | 1 × 10³ | 5 × 10² | 1 × 10² | 1 × 10 |
|---|---|---|---|---|---|---|---|---|---|
| | | | | | | | Concentration[a] | | |
| 25 | OH | OCH(CH₃)₂ | OCH(CH₃)₂ | OMe | H | 12.5[b] (80)[c] | 41.6 (80) | 79.2 (80) | 100.0 (80) |
| 26 | OH | OCH₂Ph | OCH₂Ph | OCH(CH₃)₂ | H | 11.8 (70) | 68.5 (80) | 100.0 (80) | 100.0 (80) |
| 27 | OH | OMe | OMe | OCH₂Ph | H | 43.6 (70) | 88.5 (80) | 100.0 (80) | 100.0 (80) |
| 28 | OMe | OMe | OMe | OCH₂Ph | H | 21.7 (70) | 50.2 (80) | 88.4 (80) | 100.0 (80) |
| 29 | OMe | OH | OMe | OH | H | 20.7 (80) | 30.4 (80) | 54.3 (80) | 100.0 (80) |
| 30 | OMe | OMe | OMe | OH | H | 20.4 (80) | 55.5 (80) | 72.6 (80) | 100.0 (80) |
| 31 | OH | OMe | OMe | OH | H | 28.2 (80) | 80.4 (80) | 100.0 (80) | 100.0 (80) |
| 32 | OMe | OCH(CH₃)₂ | OCH(CH₃)₂ | OCH(CH₃)₂ | H | 23.3 (80) | 54.3 (80) | 76.1 (80) | 100.0 (80) |
| 33 | OH | OCH(CH₃)₂ | OCH(CH₃)₂ | OCH(CH₃)₂ | H | 6.7 (70) | 26.6 (80) | 53.7 (80) | 87.6 (80) |
| 34 | H | OH | OH | OH | H | 0.0 (60) | 36.3 (80) | 58.4 (80) | 100.0 (80) |
| 35 | H | OH | OH | OH | OH | 0.0 (80) | 15.8 (80) | 56.4 (80) | 84.7 (80) |
| 36 | OMe | OH | OH | OH | H | 26.1 (80) | 52.2 (80) | 84.7 (80) | 100.0 (80) |

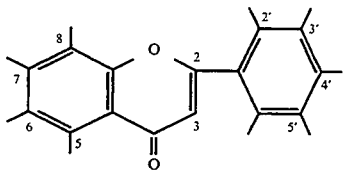

[a] Mol ratio/TPA (20 ng = 32 pMol/ml)
[b] Values represent relative percentages to the positive control value (100%).
[c] Values in parentheses are viability percentages of Raji cells.

What is claimed is:

1. A method for chemoprevention of skin tumors in mammals which comprises administering to the skin of a mammal a composition comprising a compound of the general formula

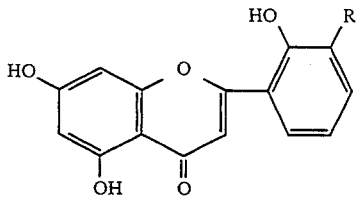

wherein R means a hydrogen atom or a hydroxyl group, as an active ingredient, and a pharmaceutical acceptable carrier, said composition being administered in an amount effective to prevent skin tumors.

2. The method of claim 1 wherein said compound is 5,7,2'-trihydroxyflavone.

3. The method of claim 1 wherein said compound is 5,7,2',3'-tetrahydroxyflavone.

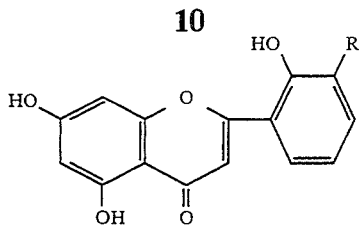

wherein R means a hydrogen atom or a hydroxyl group, as an active ingredient, and a pharmaceutical acceptable carrier, said composition being administered in an amount effective to prevent skin tumors.

2. The method of claim 1 wherein said compound is 5,7,2'-trihydroxyflavone.

3. The method of claim 1 wherein said compound is 5,7,2',3'-tetrahydroxyflavone.

* * * * *